United States Patent
Lipshaw et al.

(10) Patent No.: US 9,795,171 B2
(45) Date of Patent: Oct. 24, 2017

(54) ADJUSTABLE ELASTIC PROFILE COMPRESSION GARMENT

(71) Applicant: MEDI MANUFACTURING, INC., Whitsett, NC (US)

(72) Inventors: Moses A. Lipshaw, Encinitas, CA (US); Sandra Ann Shaw, Coronado, CA (US); Dean J. Bender, Terrell, NC (US); Thomas Richardson, Del Mar, CA (US); Teresa Kennerknecht, San Clemente, CA (US)

(73) Assignee: MEDI MANUFACTURING, INC., Whitsett, NC (US)

( * ) Notice: Subject to any disclaimer, the term of this patent is extended or adjusted under 35 U.S.C. 154(b) by 115 days.

(21) Appl. No.: 13/797,932

(22) Filed: Mar. 12, 2013

(65) Prior Publication Data
US 2013/0283500 A1 Oct. 31, 2013

Related U.S. Application Data

(60) Provisional application No. 61/609,852, filed on Mar. 12, 2012.

(51) Int. Cl.
*A41B 11/00* (2006.01)
*A61F 13/08* (2006.01)

(52) U.S. Cl.
CPC ............ *A41B 11/00* (2013.01); *A61F 13/085* (2013.01)

(58) Field of Classification Search
CPC ........ A61F 13/06; A61F 13/062; A61F 13/08; A61F 13/085; A61F 5/0104; A61F 5/0111; A41B 11/00

(Continued)

(56) References Cited

U.S. PATENT DOCUMENTS 4,198,834 A * 4/1980 Reid, Sr. .................... 66/172 E
4,215,687 A 8/1980 Shaw
(Continued)

FOREIGN PATENT DOCUMENTS

FR 2961389 12/2011
FR 2961389 A1 * 12/2011
WO 2012096950 A1 7/2012

OTHER PUBLICATIONS

PCT International Search Report, May 1, 2013.
Supplemental European Search Report in related EP Application No. EP13761669, mailed Aug. 13, 2015.

*Primary Examiner* — Kari Rodriguez
*Assistant Examiner* — Raymond E Harris
(74) *Attorney, Agent, or Firm* — Troutman Sanders LLP

(57) ABSTRACT

A compression garment, having: (a) a first portion that wraps at least partially around a body part to provide compression to the body part; and (b) a second portion that wraps at least partially around a body part; wherein the second portion is wrapped onto the first portion or is attached to the first portion such that the attachment of the second portion onto the first portion changes the elastic profile of the garment from a first elastic profile to a second elastic profile; and wherein the dimensions of the first and second portions are selected such that the relative amount of the circumference of the body part that is covered by each of the first and second portions of the garment results in a garment applying a pre-determined range of compression level fluctuation to the body part during wear.

15 Claims, 17 Drawing Sheets

(58) Field of Classification Search
USPC ........ 602/5, 23, 27, 60–65, 75–77; 128/869, 128/882; 5/239, 409
See application file for complete search history.

(56) References Cited

U.S. PATENT DOCUMENTS

| | | | | |
|---|---|---|---|---|
| 5,653,244 | A | * | 8/1997 | Shaw .......................... 128/882 |
| 5,918,602 | A | * | 7/1999 | Shaw et al. ................... 128/882 |
| 6,109,267 | A | * | 8/2000 | Shaw et al. ................... 128/882 |
| 6,338,723 | B1 | * | 1/2002 | Carpenter et al. .............. 602/75 |
| 6,684,412 | B2 | * | 2/2004 | Ricci et al. ..................... 2/240 |
| 7,103,921 | B1 | | 9/2006 | Shoemaker |
| 2005/0192524 | A1 | * | 9/2005 | Lipshaw et al. ................ 602/62 |
| 2007/0179421 | A1 | | 8/2007 | Farrow |
| 2010/0312160 | A1 | * | 12/2010 | Creighton et al. .............. 602/62 |
| 2012/0116282 | A1 | * | 5/2012 | Cros et al. ..................... 602/76 |

\* cited by examiner

ADJUSTABLE ELASTIC PROFILE COMPRESSION GARMENT

RELATED APPLICATION

The present application claims priority to U.S. Provisional Patent Application 61/609,852, entitled DYNAMIC COMPRESSION GARMENT, filed Mar. 12, 2012, the entire disclosure of which is incorporated herein by reference in its entirety for all purposes.

TECHNICAL FIELD

The present invention relates to therapeutic compression garments including compression stockings and compression wrap devices.

BACKGROUND OF THE INVENTION

Many different compression garments have been built to provide compression therapy for the treatment of circulatory disorders such as edema, lymphedema and various venous diseases. Typically, these compression garments fall into two broad categories: elastic and inelastic.

Elastic compression garments such as compression stockings, both circular and flat knit, are based on the use of elastic fibers such as spandex or latex. It is this elastic fiber that enables the stocking to provide compression and also to stretch in order to apply the stocking to the limb. Because of the elastic nature of the stocking design, stockings provide a consistent or static compression to the limb; when an individual changes position, such as moving from supine to standing, the limb circumference changes. The elastic nature of the stocking stretches to accommodate the change in circumference and maintains a fairly consistent compression level regardless of position or movement. This is particularly beneficial when a patient experiences a reduction in limb size due to the removal of excess edema in the treated limb. However it also requires that the compression stocking be removed when in a supine position (sleeping) because a consistent high compression level may result in pain in the limbs due to the decreased venous pressure.

Inelastic compression, as the name suggests, is the opposite of elastic compression in that the products do not stretch when circumference changes occur as the result of body movement. What occurs when the body is in movement is that the actual compression level under the inelastic compression system will rise and fall, thus creating a dynamic compression system. This change in compression with inelastic compression systems has been demonstrated to have dramatic effects in improved venous hemodynamics and edema reduction. Inelastic compression is achieved with Unnas boot bandages, short-stretch bandages, multi-layer bandages as well as with inelastic, adjustable wraps. These compression systems can also be worn 24 hours a day because the compression level is only at its highest when needed while standing, moving and fighting the effects of gravity on the circulatory system. The compression level is at its lowest while supine and venous pressure has decreased. While bandage systems do provide a dynamic compression effect their main drawback is that they do not adjust with reductions in the limb size and as such over the course of wear the compression level drops. This requires that the bandages be removed and reapplied quite often to maintain adequate compression for treatment. Unique systems like CircAid® Compression garments have instantly adjustable bands so the compression level can be easily adjusted to accommodate changes in limb volume.

In recent years a measurement of the elasticity or stiffness of a compression system has been accepted and is referred to as the Static Stiffness Index. The Static Stiffness Index (SSI) is defined as the absolute change in compression applied to the limb by the compression garment when the user changes posture from the standing to supine position. The pressure applied while standing is often termed working pressure and while supine is termed resting pressure. Systems with an absolute working-resting pressure difference of less than 10 mmHg are qualified as elastic systems. Those with a difference greater than 10 mmHg are considered inelastic systems.

All compression systems can now be defined by not only the absolute compression level they provide but also by amount that the compression level fluctuates during activity or Static Stiffness Index. For example an elastic stocking may provide a compression level of 20-30 mmHg but has an SSI of 5 mmHg, whereas an inelastic wrap may also provide a compression level of 20-30 mmHg but have an SSI of 20 mmHg. It has been proven that therapeutic differences exist between these two systems. While the elastic system may be more preferable to the user because it is more consistent with limb volume changes and requires less adjustments, their condition may dictate the need for improved circulatory performance provided by the inelastic garment. If a compression garment existed that provided 20-30 mmHg and a SSI of 10 mmHg perhaps this would be the best combination of benefits for this particular patient. However, this compression garment may not exist forcing a decision to be made from the garments available.

To date by in large most products have only been defined and prescribed by the target compression level they provide and generically termed elastic or inelastic. The working and resting pressure levels they provide cannot be changed. Some compression garments have been designed to provide instantly adjustable compression levels to accommodate multiple prescription compression levels but the Static Stiffness Index of these garments remains relatively unchanged. A compression system has yet to be designed where the user can instantly adjust the static stiffness index in the garment or a portion of the garment to a prescribed level to meet their unique needs.

SUMMARY OF THE INVENTION

Broadly speaking, the present invention provides a compression garment made of a first material with an initial elasticity profile and compression fluctuation range. A second material is added to the first material, thereby instantly changing the elasticity profile. This in turn instantly changes the range of compression fluctuation the garment applies to the patient's limb during normal wear (e.g.: as the circumference of a leg changes from lying down to standing).

In preferred aspects, the present invention provides a compression garment, comprising: (a) a first portion that wraps at least partially around a body part to provide compression to the body part; and (b) a second portion that wraps at least partially around a body part. The second portion is wrapped on top of the first portion (i.e.: applied in parallel) or is attached in series to the first portion such that the attachment of the second portion onto the first portion changes the elasticity profile of the garment from a first elasticity profile to a second elasticity profile. In addition, during design, the dimensions of the first and second portions are selected such that the relative amount of the circumference of the body part that is covered by each of the first and second portions of the garment results in a garment applying a pre-determined range of compression level fluctuation to the body part when the garment is stretched to fit around the body part during normal wear (i.e.: as the body part changes in diameter as the posture of the patient changes).

In the simplest form, the first portion may be elastic, and the second portion may be inelastic. As a result, adding the second portion onto the first portion preferably makes the garment stiffer and less elastic. It is to be understood that the present invention is not limited to specific elasticities or inelasticities for each of the first and second portions. Typically, they will be different (with the second portion being less elastic), but they may be the same (with the addition of the second portion in parallel simply making the garment thicker and thus less elastic). The second portion is preferably held onto the first portion by hook and loop fasteners, or it may be sewn or glued into position.

In accordance with the present invention, the elasticity profile of the garment is determined by altering the ratio of at least two fabrics differing in elasticity. Since the compression level is known when fabric tension and limb circumference are known, therefore a circumference scale translates a stretched distance into an applied compression level. This provides a method of designing the garment such that it provides a known, predictable, pre-determined range of compression level fluctuation to the patient's limb as their limb increases and decreases in circumference during wear.

The present invention can be provided in various embodiments such as a stocking/glove or as a "compression wrap" (being a device with bands extending therefrom for wrapping around the limb).

In preferred embodiments, the first portion comprises indicia thereon, and the placement of the indicia on the garment is calibrated such that when the second portion (such as a strap, flap or fold) is aligned with the indicia, the compression garment provides the known pre-determined compression fluctuation range to the body part.

Optionally, the indicia may comprise two or more sets of indicia, with each set corresponding to a different pre-determined compression fluctuation range. Thus, a user can change from one known range of compression level fluctuation to another known range of compression level fluctuation simply by moving the second portion from one set of indicia to another. The first end of the second portion may be fixed to the first portion and a second end of the second portion is releasably attached to the elastic portion by hook and loop fasteners. In addition, the indicia may be put on the second portion rather than the first portion.

Optionally, the width of the second portion can vary along the length of the compression garment, providing different ranges of compression fluctuations along the length of the garment. In various embodiments, the second portion may extend partially but not fully along the length of the first portion of the compression garment.

In its various embodiments, the present invention provides a compression garment with a compression level fluctuation range that is accurately known; and preferably can be easily adjusted between two or more known compression level fluctuation ranges. In preferred embodiments, multiple defined engagement points on the adjustable portion of the sleeve indicate the compression level fluctuation range.

In one embodiment, the present invention provides a compression socking that is easy to put on in which known compression level fluctuation range can be adjusted to a new range level per the user's preference. Stockings most often provide a static compression level throughout the garment where the working and resting pressures vary little from the base compression level the garment is intended to provide. It may be preferred to increase working pressure and compression level fluctuation range in only the calf region to create a massaging or pumping fluctuating pressure effect to further induce venous blood flow.

In another embodiment, the present invention provides compression wrap having a mid-section with bands extending therefrom. Since the relative ratios of the first and second portions of the garment are known when the garment is designed, the garment provides a known, predictable range of dynamic compression force fluctuation when wrapped around the limb. The elasticity of either portion could altered to change the magnitude of the pressure fluctuation experienced during wear.

In another embodiment the invention provides an inflatable compression device where the pressure fluctuations are induce pneumatically rather than natural circumference changes of the limb during movement. The ratios of the first and second portions are designed or changed to provide predictable ranges of compression fluctuations to the limb as the device inflates and deflates.

The present invention also provides a method of designing a compression garment, comprising: (a) providing a first portion that wraps at least partially around a body part to provide compression to the body part, the first portion having a first elasticity profile and applying a first range of compression level fluctuation to the body part; and (b) attaching a second portion onto the first portion. This changes the elasticity profile of the garment from the first elasticity profile to a second elasticity profile thereby changing the range of compression level fluctuation applied by the garment from the first range of compression level fluctuation to a second range of compression level fluctuation.

In this method, the width of the second portion is chosen such that the relative percentage of the circumference of the first portion that is covered by the second portion is chosen such that the distance to which the first portion is stretched in circumference to fit around the body part provides a pre-determined range of compression force fluctuation to the body part. During the initial design process, increasing the chosen width of the second portion increases the pre-determined compression force fluctuation to the body part, while decreasing the chosen width of the second portion would decrease the pre-determined compression force fluctuation to the body part.

BRIEF DESCRIPTION OF THE DRAWINGS

FIGS. 1A to 3 illustrate stretching and compression properties of various elastic and non-elastic materials, as follows.

FIG. 1A is a schematic illustration of an elastic fabric compression garment wrapped into a cylindrical shape (prior to being wrapped around a patient's limb).

FIG. 3 illustrates the tension and stretching properties of an elastic compression garment as compared to an elastic compression garment having a non-elastic section attached thereon.

FIG. 4A-1 illustrates the range of compression levels applied to a body part by an elastic compression garment when a user is lying down. FIG. 4A-2 illustrates the range of compression levels applied to a body part by the same garment when the user is standing. FIG. 4A-3 is a graph comparing the normal range of compression levels applied to the body part in the configurations of FIGS. 4A-1 and 4A-2.

FIG. 4B-1 illustrates the range of compression levels applied to a body part by an elastic compression garment that is partially covered by an inelastic wrap when a user is lying down. FIG. 4B-2 illustrates the range of compression levels applied to a body part by the same garment when the user is standing. FIG. 4B-3 is a graph comparing the normal range of compression levels applied to the body part in the configurations of FIGS. 4B-1 and 4B-2.

FIG. 4C-1 is similar to FIG. 4B-1, by a larger portion of the elastic compression garment is covered by an inelastic wrap. FIG. 4C-1 illustrates the range of compression levels applied to a body part by an elastic compression garment that is partially covered by an inelastic wrap when a user is lying down. FIG. 4C-2 illustrates the range of compression levels applied to a body part by the same garment when the user is standing. FIG. 4C-3 is a graph comparing the normal range of compression levels applied to the body part in the configurations of FIGS. 4C-1 and 4C-2.

FIG. 7 illustrates a standard elastic compression wrap having bands extending therefrom, prior to placement around a patient's limb.

FIG. 8 is the compression wrap of FIG. 7, after it has been wrapped around a patient's leg.

FIG. 9 illustrates the standard elastic compression wrap of FIG. 7, but with a narrow non-elastic portion attached thereon.

FIG. 10 is a side elevation view corresponding to FIG. 9.

FIG. 11 illustrates the standard elastic compression wrap of FIG. 7, but with a wide non-elastic portion attached thereon.

FIG. 12 is a side elevation view corresponding to FIG. 11.

FIG. 13 illustrates the standard elastic compression wrap of FIG. 7, but with a tapered non-elastic portion attached thereon.

FIG. 14 is a side elevation view corresponding to FIG. 13.

FIG. 15 is an illustration similar to FIG. 13, but with the tapering reversed in direction.

FIG. 16 is a side elevation view corresponding to FIG. 15.

FIG. 17 illustrates a compression wrap having two opposite first portions with a second portion spanning therebetween, showing the first and second portions linked in series around the circumference of the garment.

FIG. 18 is a side elevation view corresponding to FIG. 17.

FIG. 19 illustrates a compression wrap having a second portion that does not extend from the top to bottom of the garment.

FIG. 20 is a side elevation view corresponding to FIG. 19.

FIG. 21 illustrates a compression wrap having three layers of material extending the full top to bottom length of the garment.

FIG. 22 is a side elevation view corresponding to FIG. 21.

FIG. 23 illustrates a compression wrap having three layers of material, with each of the three materials extending to different top to bottom lengths along the garment.

FIG. 24 is a side elevation view corresponding to FIG. 23.

FIG. 25 illustrates a compression wrap having a curved second portion.

FIG. 26 is a side elevation view corresponding to FIG. 27.

FIG. 27 illustrates a compression wrap having a second portion spanning the full width of the first portion.

FIG. 28 is a side elevation view corresponding to FIG. 27.

FIG. 29 illustrates a compression wrap having a small second portion

FIG. 30 is a side elevation view corresponding to FIG. 29.

FIG. 31 illustrates a compression wrap having a three small second portions applied in series next to one another.

FIG. 32. is a side elevation view corresponding to FIG. 31.

FIG. 33 illustrates a compression wrap having bands made of a first material and a main body section made of a different material.

FIG. 34 is a side elevation view of FIG. 35.

FIG. 35 is a compression wrap similar to FIG. 33, but with a triangular shaped portion added thereto.

FIG. 36 is a side elevation view corresponding to FIG. 35.

FIG. 37 illustrates a compression wrap with a pair of positioning indicia on the second portion.

FIG. 38 is a side elevation view of FIG. 37.

FIG. 39 illustrates a compression wrap with a single set of positioning indicia on the second portion after one set of indicia on the second portion has been trimmed away.

FIG. 40 is a side elevation view of FIG. 39.

FIG. 41 illustrates a compression wrap with positioning indicia thereon.

FIG. 42 is a side elevation view of FIG. 41.

FIG. 43 illustrates a compression wrap with positioning indicia on the first portion, and a second portion added thereto.

FIG. 44 is a side elevation view of FIG. 43.

DETAILED DESCRIPTION OF THE DRAWINGS

FIGS. 1A to 3 illustrate stretching and compression properties of various elastic and non-elastic materials found in compression garments that are wrapped around a patient's limb. Skin compression levels applied by the garments are determined by the stretch characteristics of the material, the circumference of the garment and the circumference of the limb to which it is applied. The resulting skin surface pressure can be approximated via La Place's law for a cylinder which states that:

$$T = Pr$$

where
T=the wall tension in the cylinder,
P=the internal pressure, and
r=the radius of the cylinder.

For therapeutic compression garments, the wall tension in the cylinder (T) is the degree to which the material of the cylindrical garment is stretched around the limb. Thus, for a constant radius limb, the compression pressure on the limb is increased by stretching the garment. As will be shown, the tension in the garment can be increased by stretching (either by increasing the radius of the limb, or by shortening the garment by pulling it over upon itself.

Figure 1A:
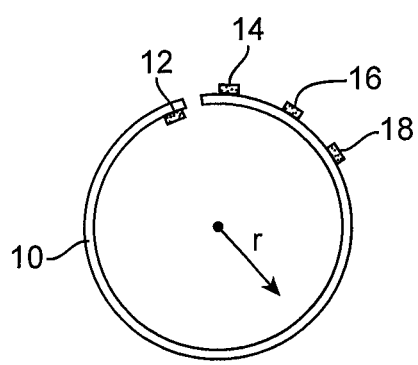

FIGS. 1A to 1D illustrate this as follows. An compression garment 10 is wrapped around a limb L. FIG. 1A shown the garment prior to use. Garment 10 has hook and loop fasteners 12, 14, 16 and 18. In FIG. 1A, there is no tension in the garment, and no inward pressure (since the limb L has not yet been inserted therein).

Figure 1B:
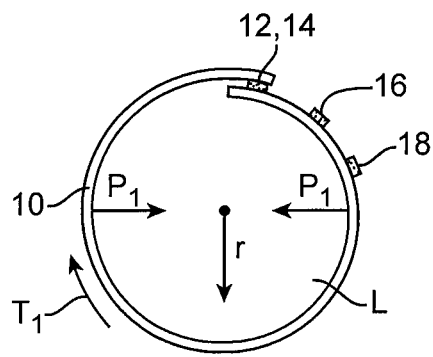
FIG. 1B is a schematic illustration corresponding to FIG. 1A, after the garment has been stretched around a limb and attached to itself at a first position.

In FIG. 1B, garment 10 is now wrapped and stretched somewhat to fit around limb L, and fastener 12 is connected onto fastener 14. The stretching in the garment increases the wall tension to T1. This in turn increases the compression pressure on the limb to P1.

Figure 1C:
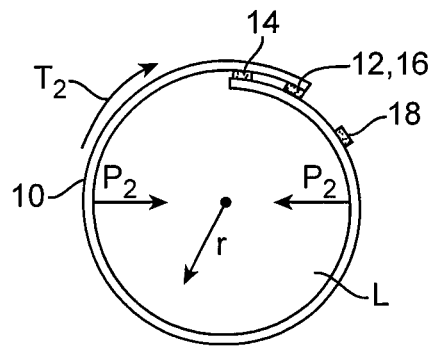
FIG. 1C is a schematic illustration corresponding to FIG. 1A, after the garment has been further stretched around a limb and attached to itself at a second position.

In FIG. 1C, garment 10 is stretched more tightly around the limb such that fastener 12 now connects to fastener 16. Thus, the tension in the garment is increased from T1 to T2, and correspondingly the inward pressure on the limb is increased from P1 to P2. FIG. 1l) shows even further stretching of the garment where fastener 12 is now connected onto fastener 18. Tension is thus further increased to T3, and the corresponding inward radial pressure on the limb is increased to P3.

Figure 1D:
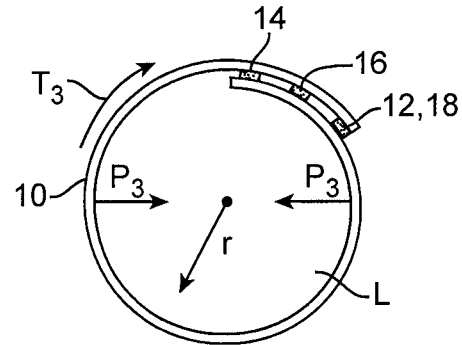
FIG. 1D is a schematic illustration corresponding to FIG. 1A, after the garment has been even further stretched around a limb and attached to itself at a third position.

As can be seen in FIGS. 1B to 1D, increasing the tension T in the garment (i.e.: stretching the garment) increases the inward radial pressure P when the radius of the limb is kept constant. Per La Place's law for a cylinder, the inward pressure P would also increase if the radius of the limb increased causing the tension in the material to increase at a higher proportion than the radius increase, or decrease should the radius of the limb decrease and the tension in the material decreases at a higher proportion than the radius.

Figure 2A:
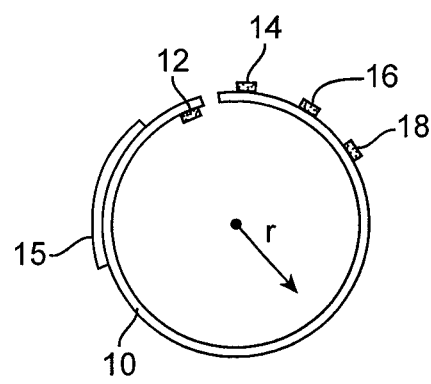
FIG. 2A is a schematic illustration of an elastic fabric compression garment having a non-elastic section attached thereto, wrapped into a cylindrical shape (prior to being wrapped around a patient's limb).

FIGS. 2A to 2D are similar to FIGS. 1A to 1D, but now a non-elastic strap 15 has been affixed onto elastic compression garment 10. FIG. 2A shows the garment prior to use. There is no tension in the garment, and no inward pressure (since the limb L has not yet been inserted therein).

Figure 2B:
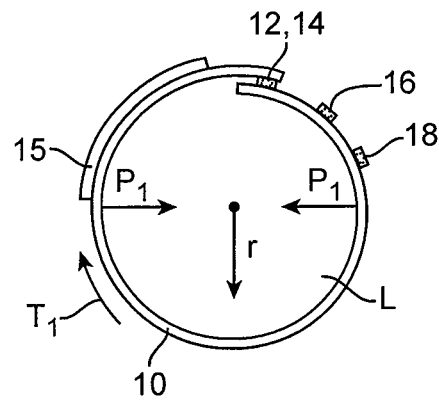
FIG. 2B is a schematic illustration corresponding to FIG. 2A, after the garment has been stretched around a limb and attached to itself at a first position.

In FIG. 2B, garment 10 is wrapped and stretched somewhat to fit around limb L, and fastener 12 is connected onto fastener 14. The portion of elastic garment 10 that is covered by non-elastic portion 15 will stretch inelastically (i.e.: it will remain generally stiff, and stretch very little, if at all). The stretching in the remaining portion of the garment 10 that is not covered by inelastic portion 15 increases the wall tension to T1. This in turn increases the compression pressure on the limb to P1. Importantly, since there is less elastic material to stretch (as compared to FIG. 1 where the entire circumference was elastic), the Tension T1 in FIG. 2B will be higher than the tension T1 in FIG. 1B.

Figure 2C:
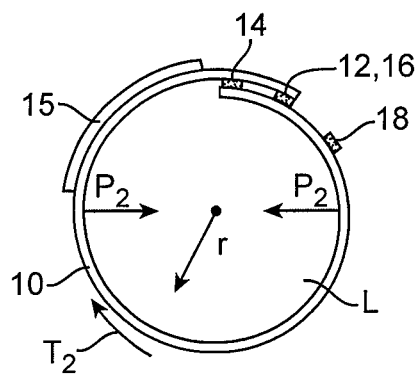
FIG. 2C is a schematic illustration corresponding to FIG. 2A, after the garment has been further stretched around a limb and attached to itself at a second position.
Figure 2D:
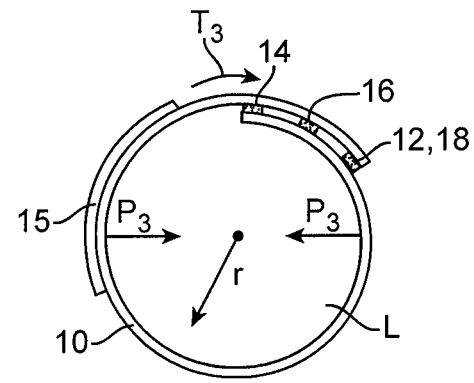
FIG. 2D is a schematic illustration corresponding to FIG. 2A, after the garment has been even further stretched around a limb and attached to itself at a third position.

FIGS. 2C and 2D show garment 10 being stretched more tightly around the limb such that fastener 12 now connects to fastener 16 and 18 respectively. Thus, the tension in the garment is increased from T2 to T3, and correspondingly the inward pressure on the limb is increased from P2 to P3. The presence of inelastic strap 15 will ensure that the tension in FIG. 2C is greater than that in FIG. 1C, and that the inward compression P2 in FIG. 2C is greater than that in FIG. 1C.

Figures 1, 4A:
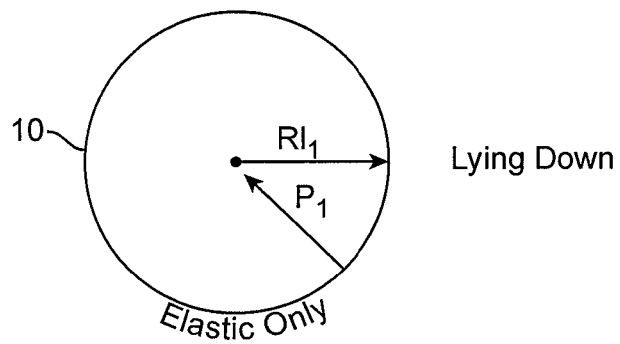
Figures 2, 4A:
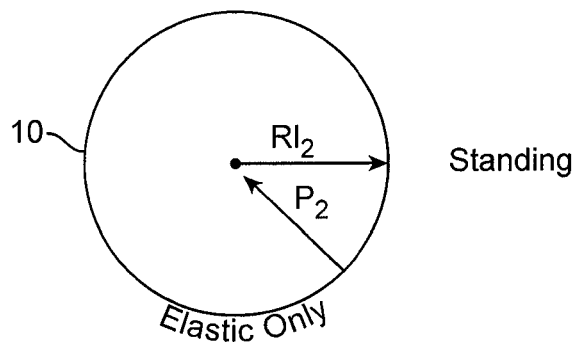
Figures 3, 4A:
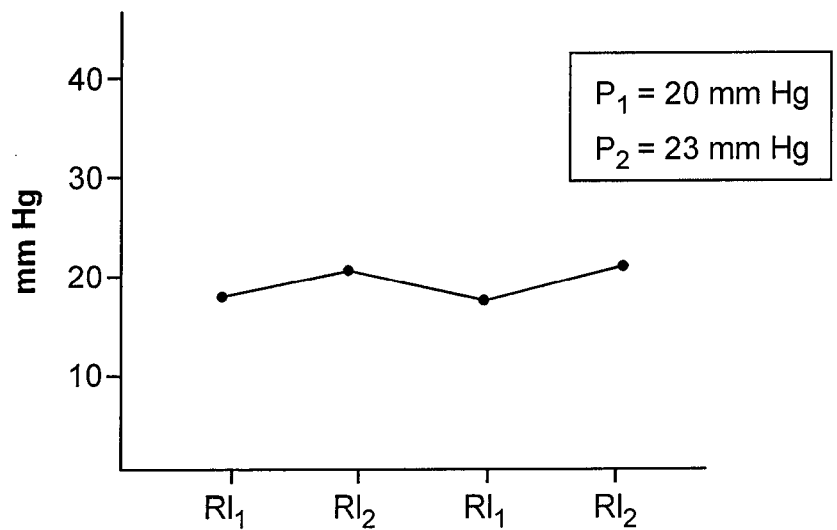

FIGS. 1 and 2 illustrate an important feature of the present invention, being that the selection of the amount of the circumference of elastic garment 10 that is to be covered by non-elastic portion 15 determines the stiffness of the garment assembly. Should the designer (or user) attach a more narrow band 15 (wrapping around less of the circumference of the body limb), the overall garment assembly will be more elastic. Conversely, should the designer (or user) attach a more wide band 15 (wrapping around more of the circumference of the body limb), the overall garment assembly will be less elastic. The present invention thus encompasses the design of a compression garment in which the relative percentages of the circumference that are elastic and non-elastic is selected to apply a desired compression force or profile for a given limb circumference.

This is because the tension force in a compression fabric is directly proportional to the percentage of stretch created within the fabric (i.e.: the length the fabric is stretched). Therefore, as the elastic material length is reduced, the percentage of stretch and force in the material increases. This increase in tension force increases the pressure applied to the limb. If the elastic material's stretch/force characteristics are known, the range of pressures can be calculated for different limb circumferences and the tension force can be adjusted as needed to define compression levels for a specific limb circumference and thus the amount of fluctuation between compression levels caused by the limb changes in circumference can be altered. By varying the ratio of the elastic to non-elastic material, a range of applied compression level fluctuations can be generated.

Moreover, if indicia are placed at each of fastener locations 14, 16 and 18, the approximate base compression level for a known degree of stretch of the garment can be calibrated. Thus, the patient knows what approximate compression force will be on their limb when it is closed to each of the positions of fastener 14, 16 and 18. It is to be understood, however, that the precise compression level will depend upon both the actual circumference of the leg (which changes during the day), and the stiffness profile of the garment. Note: the present invention is directed primarily to changing the overall elasticity profile of the garment, not to varying the approximate base compression level the garment offers.

Figure 3:
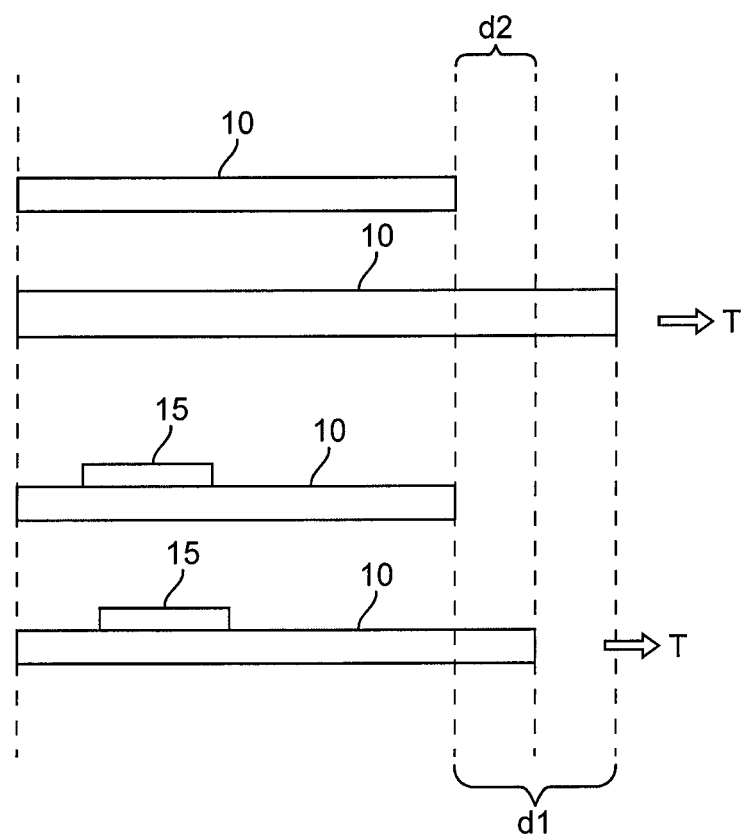

FIG. 3 illustrates the tension and stretching properties of the garments of FIGS. 1 and 2 laid flat, with tension applied thereto. From top to bottom as seen in the figure, the elastic portion 10 is shown with no tension applied. Below that, the same elastic portion 10 is shown with a tension T applied (such that it's end stretches to distance d1). Below that, an elastic portion 10 is shown with an inelastic portion affixed thereon and no tension applied. Below that, the portions 10 and 15 are shown with the same tension T applied thereto. As can be seen, portion 15 does not stretch (nor does the portion of 10 directly thereunder). As a result, the garment only stretches to position d2. As can be appreciated, adding non-elastic portion 15 onto elastic portion 10 makes the overall garment assembly stiffer or less elastic (and more resistant to stretching).

FIGS. 4A-1 to 4C-3 illustrate the normal range of compression levels applied to a body part by an elastic garment; an elastic garment that is partially covered by a short inelastic wrap; and an elastic garment that is partially covered by a longer inelastic wrap respectively, as follows.

FIGS. 4A-1 and 4A-2 shows an elastic garment wrapped around the leg when the user is standing up or lying down. During normal daily wear of the elastic garment, leg circumference changes. For example, when lying down in FIG. 4A-1, the leg will have a (smaller) radius of R11. The compression force on the leg will be P1. When standing in FIG. 4A-2, the leg will have a (larger) radius of R12. The compression force on the leg will then be P2. Since garment 10 is highly elastic, it will readily stretch to accommodate the changes in diameter in the leg. As a result, the pressure P1 while lying down (i.e.: 20 mmHg) may be increased only slightly to P2 while standing (i.e.: 23 mmHG). Thus, the range of compression applied to the leg will only change within a small range (i.e.: 3 mmHG) during the day.

Figures 1, 4B:
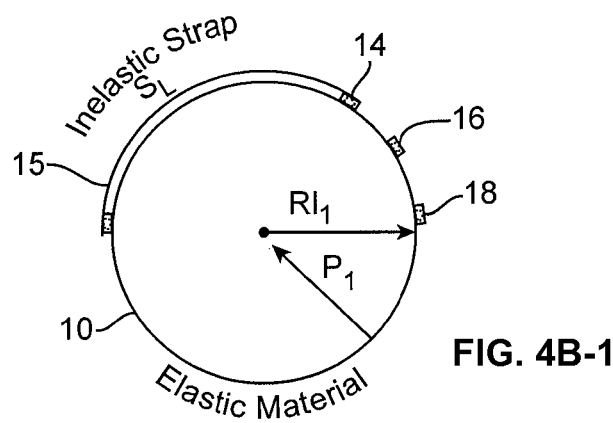
Figures 2, 4B:
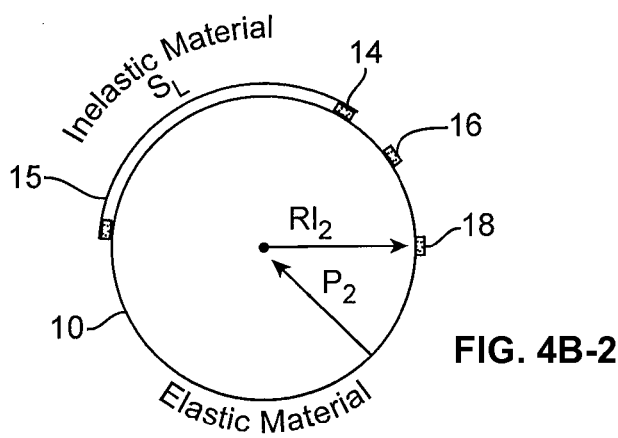
Figures 3, 4B:
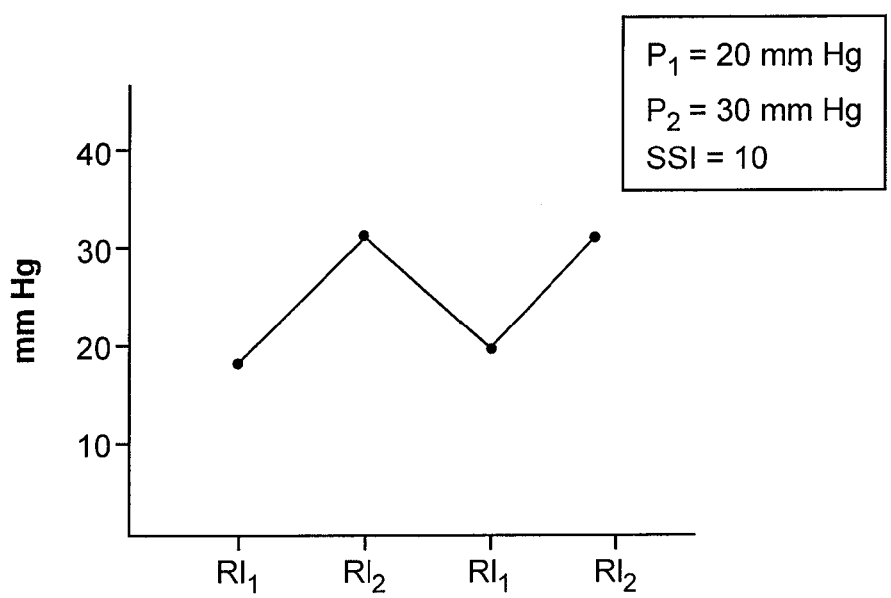

FIGS. 4B-1 and 4B-2 show a short inelastic strap 15 attached to elastic portion 10. Adding second portion 15 after the garment is donned makes the garment less elastic, now having a higher stiffness profile. In this case, the base compression level applied to the patient is the same (20 mmHg). However, the pressure while standing P2 has now increased (i.e. 30 mmHg). The range of compression applied will now fluctuate more greatly during the day (10 mmHg). FIGS. 4B-1 through 4B-3 thus illustrates an important feature of the present invention—instantly changing the range of compression level fluctuation applied to the limb by changing the elasticity profile of the garment by attaching a second portion of material to a first portion of material.

Figures 1, 4C:
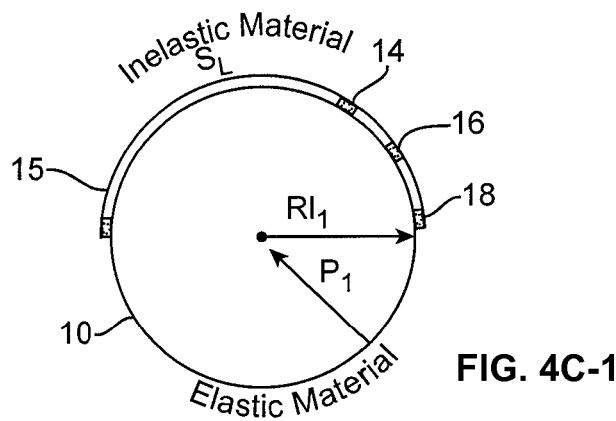
Figures 2, 4C:
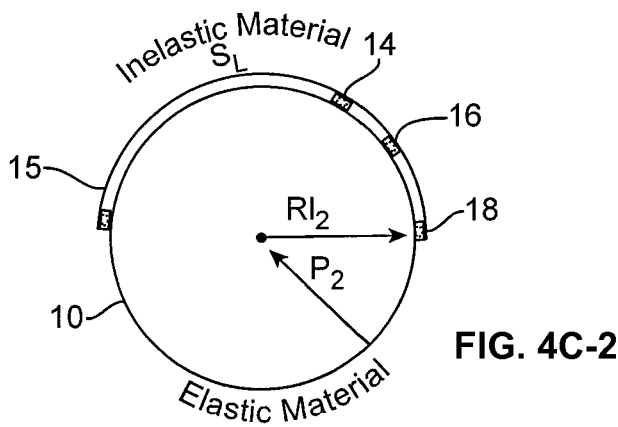
Figures 3, 4C:
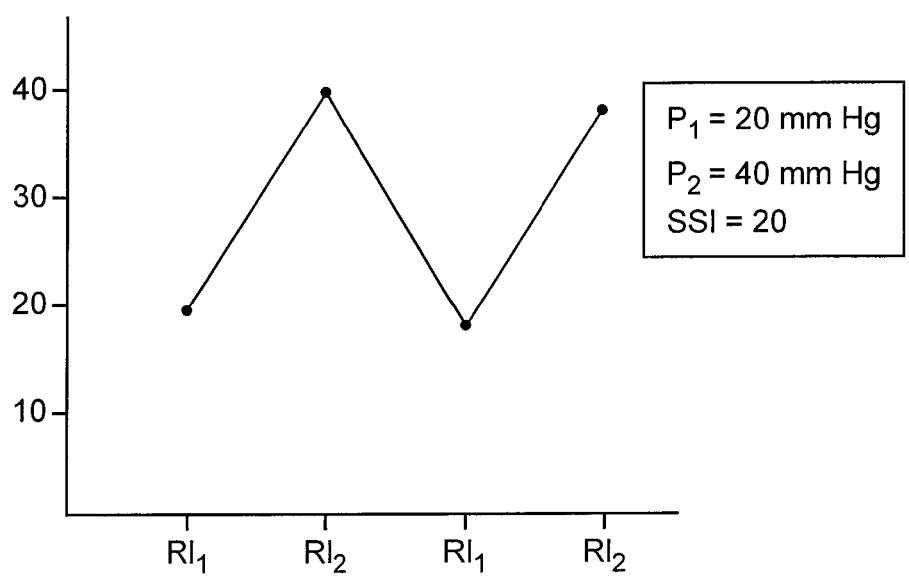

Finally, in FIGS. 4C-1 and 4C-2, the elastic portion 10 is stretched by moving inelastic portion 15 from the position of fastener 14 to 18. This will increase the range of compression applied to the leg to from 20 to 40 mmHG). The base pressure remains the same at 20 mHg as in FIGS. 4A-1 through 4B-3. FIGS. 4C-1 through 4C-3 show that adding more inelastic material (by fastening to fastener 18) increases the fluctuation range to 20 mmHG (i.e. 40 mmHg-20 mmHg=20 mmHg). This is even greater than seen in FIGS. 4A-1 through 4B-3.

The order of operations will have an effect on the base pressure. Hypothetically if the inelastic material 15 is added before the garment is donned the base pressure will increase along with an increased pressure fluctuation range. This is important because the addition of the second portion 15 before or after donning determines if it modifies the base level of compression and the range of compression level fluctuation or only the range of compression level fluctuation.

FIGS. 5A to 6B illustrate various embodiments of the present invention, as incorporated into elastic compression stockings, as follows.

Figure 5A:
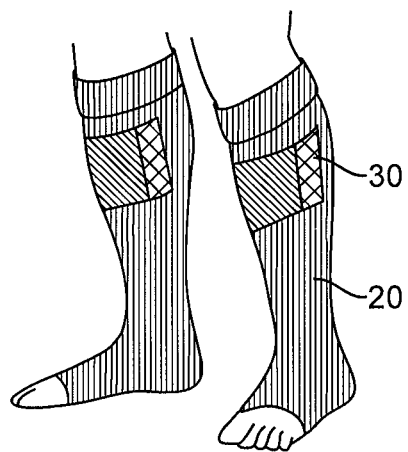
FIG. 5A illustrates an elastic compression stocking having a single non-elastic flap attached at the calf.
Figure 5B:
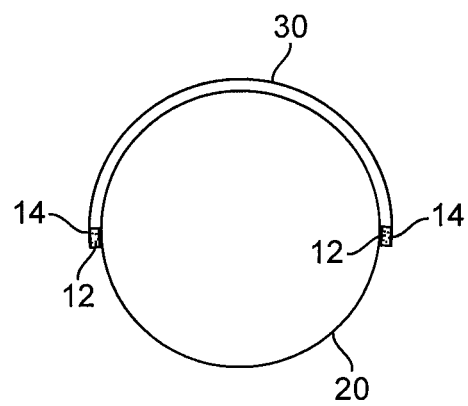
FIG. 5B is a sectional plan view through the compression stocking of FIG. 5A at the calf location.

FIG. 5A illustrates an elastic compression stocking having a single non-elastic flap 30 attached at the calf. FIG. 5B is a sectional plan view through the compression stocking at the calf. In use, the user first pulls on the stocking and then attaches the non-elastic flap 30 (by attaching fasteners 12 on elastic garment 20 to fasteners 14 on non-elastic strap 30). The addition of second portion 30 changes the stiffness profile of the garment, making it stiffer and less elastic, thereby providing a higher range of compression force fluctuation to the calf. This provides additional stiffness (especially as the calf flexes during walking).

Figure 6A:
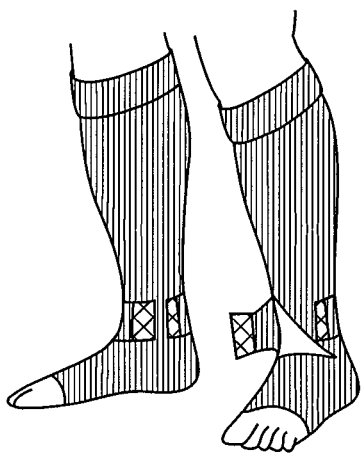
FIG. 6A illustrates an elastic compression stocking having an opening that is covered by a single inelastic strap that is fastened back upon itself.
Figure 6B:
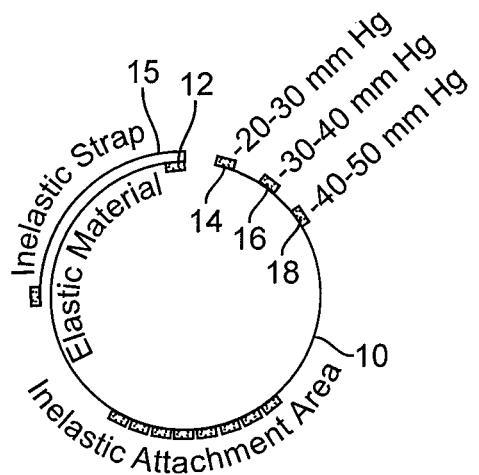
FIG. 6B is a sectional plan view through the compression stocking of FIG. 6A.

FIG. 6A illustrates an elastic first portion 10 with an inelastic second portion 15 attached thereon. The addition of inelastic portion 15 to elastic portion 10 increases the range of compression forces applied to the limb. In addition, by stretching the elastic portion 10 to be fastened at locations 14, 16 or 18, the range of compression forces applied can be increased. For example, when fastener 12 is attached to fastener 14, the garment may apply a compression force of 20 to 30 mmHG. When fastener 12 is applied to fastener 16, the garment may apply a compression force of 30 to 40 mmHG. Lastly, when fastener 12 is applied to fastener 18, the garment may apply a compression force of 40 to 50 mmHG. These pressure ranges are the applied base level of compression and are not to be confused with the compression range fluctuations related to the stiffness of the garment. Once the garment is donned the inelastic portion can then be wrapped and attached to the inelastic attachment area to change the elasticity profile of the garment and induce greater compression level fluctuations over the course of wear.

FIGS. 7 to 44 illustrate various embodiments of the present invention, as incorporated into compression wraps, as follows.

Figure 7:
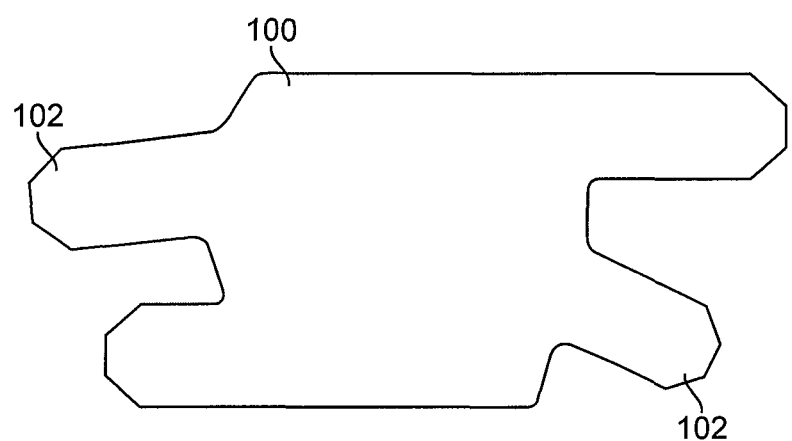
FIGS. 7 to 44 illustrate various embodiments of the present invention, as incorporated into compression wrap garments, as follows.
Figure 8:
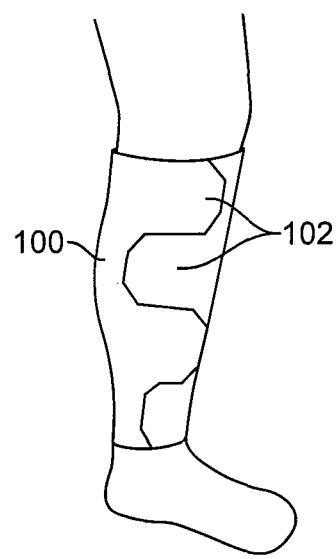

FIG. 7 is a illustrates a standard compression wrap 100 having bands 102 extending therefrom, prior to placement around a patient's limb. FIG. 8 is the compression wrap of FIG. 7, after it has been wrapped around a patient's leg (showing bands 102 juxtaposed between one another).

Figure 9:
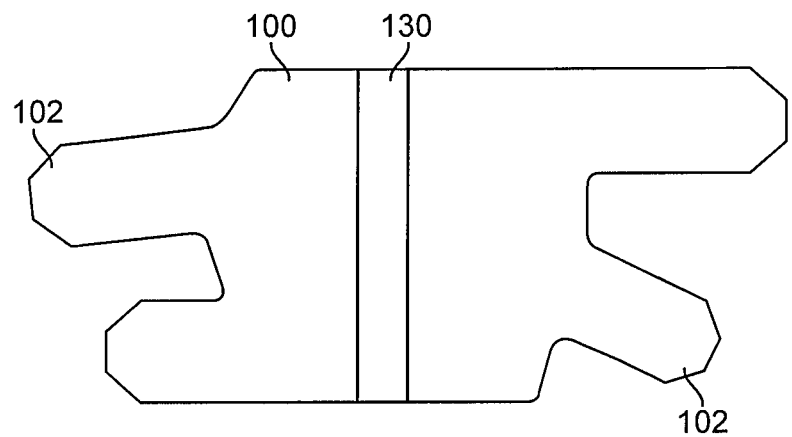
Figure 10:
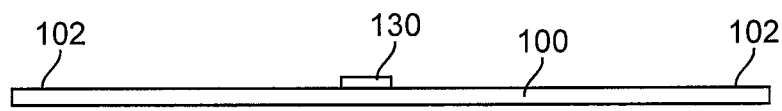

FIG. 9 illustrates the standard compression wrap of FIG. 7, but with a narrow non-elastic portion 130 now attached thereon to reduce the elasticity throughout the length of the garment and induce greater compression level fluctuations during wear compared to FIG. 7. As seen in FIG. 10, non-elastic portion 130 may be attached to elastic portion 100 by hook and loop fasteners. Alternatively, it may be sewn or glued in place.

Figure 11:
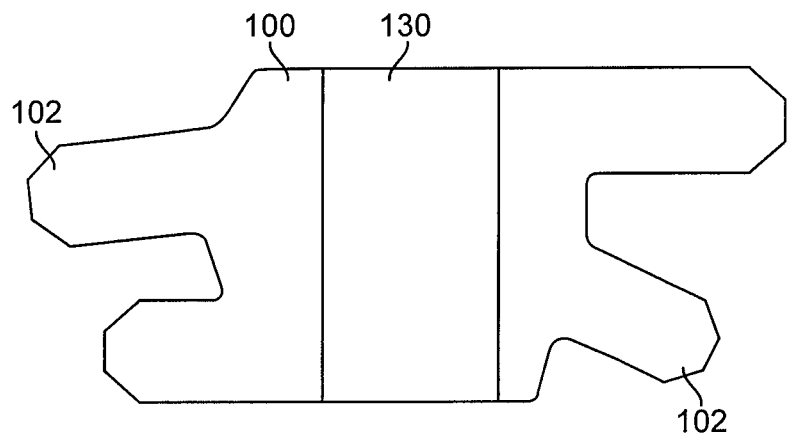
Figure 12:
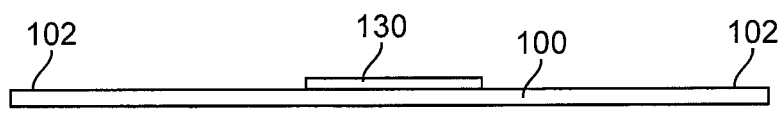

FIG. 11 illustrates the standard compression wrap of FIG. 7, but with a wider non-elastic portion 130 attached thereon instead to further reduce the elasticity throughout the length of the garment and increase the compression level fluctuations during wear compared to FIGS. 7 and 9. As can be appreciated, the garment assembly in FIG. 11 will be stiffer than the garment assembly in FIG. 9.

Figure 13:
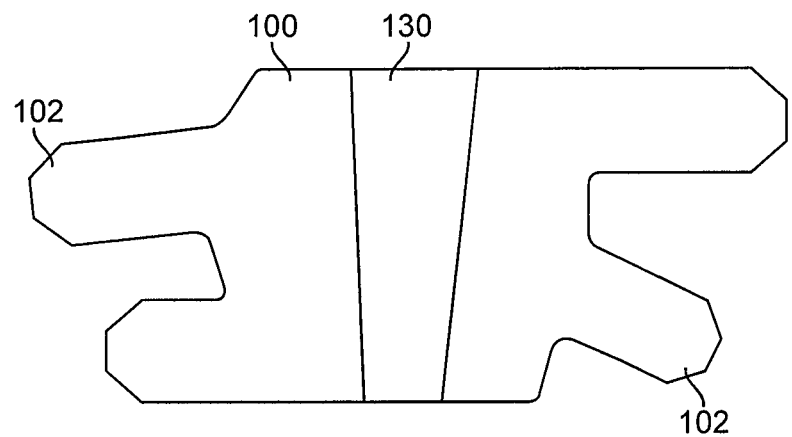
Figure 14:
Figure 15:
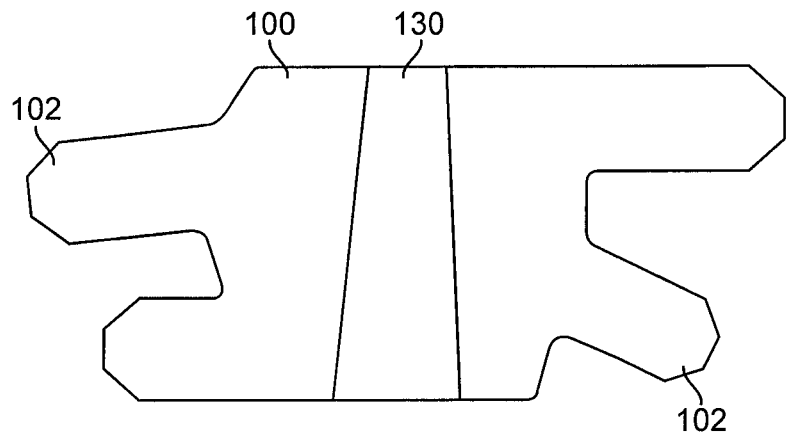
Figure 16:
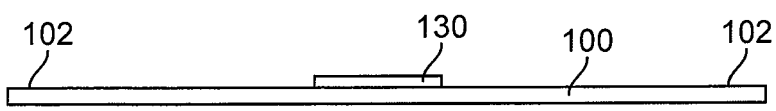

FIG. 13 illustrates the standard elastic compression wrap of FIG. 7, but with a tapered non-elastic portion attached thereon. This garment will be stiffer at the top (i.e.: the end where non-elastic portion 130 is widest), and less stiff at the bottom (i.e.: the end where non-elastic portion 130 is narrowest). Greater compression level fluctuations will be experienced during wear at the top of the garment than the bottom. FIG. 14 is a side view. FIG. 15 is an embodiment with the tapering going the other way. In FIG. 15, the garment will be most elastic at the top and least elastic at the bottom. FIG. 16 is a side view of FIG. 15. Greater compression level fluctuations will be experienced during wear at the bottom of the garment than the top.

Figure 17:
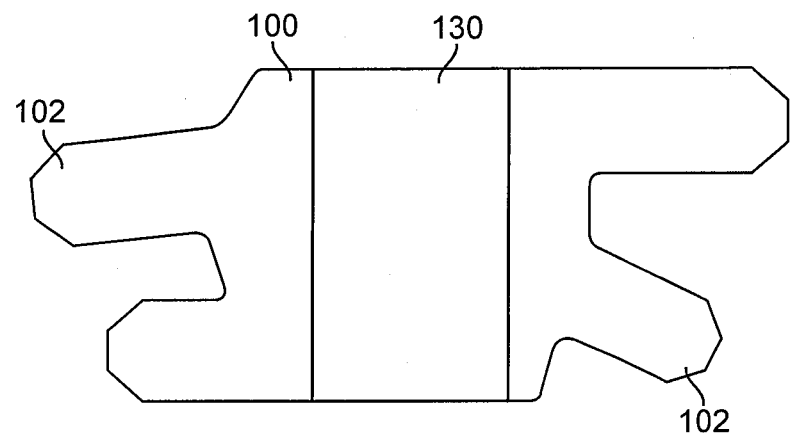
Figure 18:
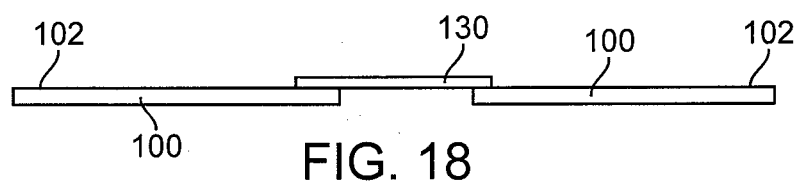

FIG. 17 shows an embodiment with two first portions 100 with a second portion 130 spanning therebetween. In this embodiment, portions 100 and 130 act in series rather than in parallel. FIG. 18 is a side view.

Figure 19:
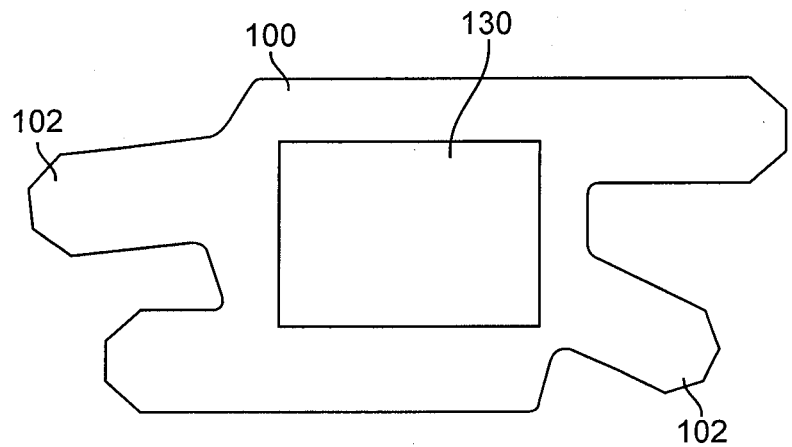
Figure 20:
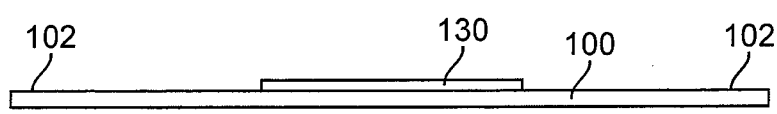

FIG. 19 is an embodiment with a stiff second portion 130 positioned at its mid-section. The top and bottom ends of this garment will be more elastic than its mid-section. FIG. 20 is a side view.

Figure 21:
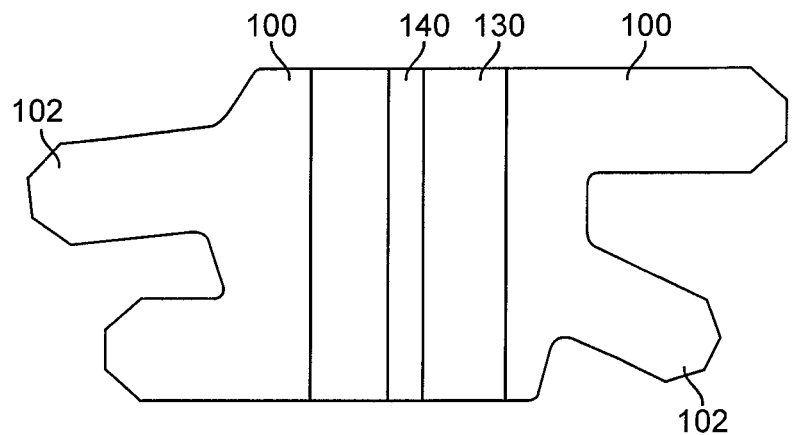
Figure 22:
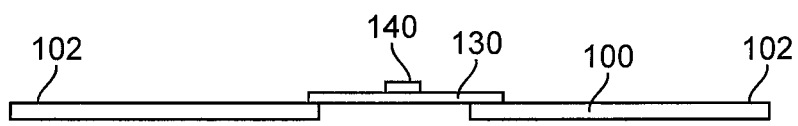

FIG. 21 shows an embodiment with three portions of material. Portion 140 is added onto portion 130, thus increasing the stiffness profile from that seen in FIG. 17. FIG. 22 is a side view.

Figure 23:
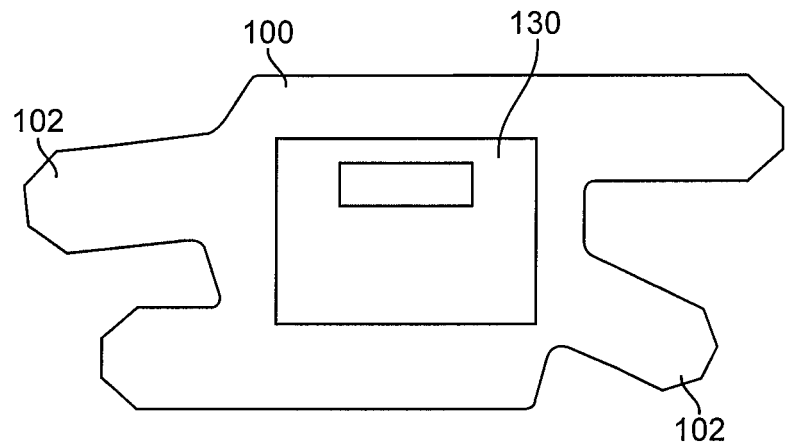
Figure 24:
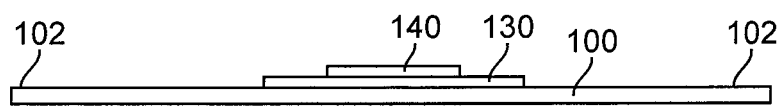

FIG. 23 is comparable to the embodiment of FIG. 21, but the three portions do not run the entire top to bottom length of the garment. FIG. 24 is a side view.

Figure 25:
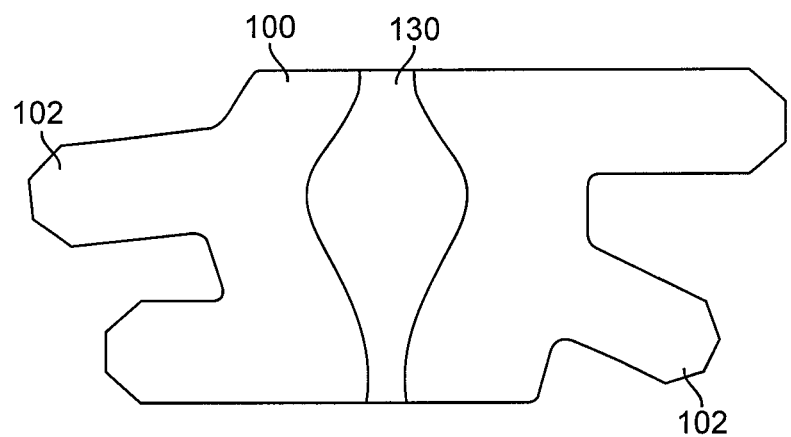
Figure 26:
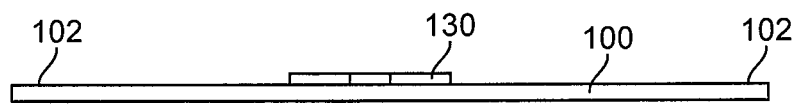

FIG. 25 is an embodiment with a curved portion 130. The garment is stiffest in the regions where portion 130 is widest. FIG. 26 is a side view. Alternatively the first portion of the material 100 could be inelastic and the material of 130 elastic. This reverses the elasticity profile.

Figure 27:
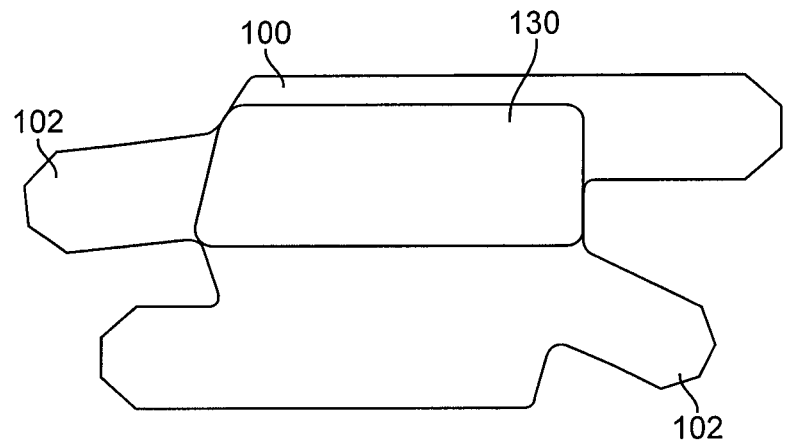
Figure 28:
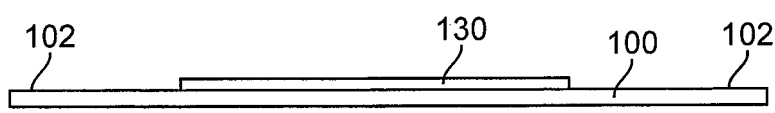

FIG. 27 is an embodiment with second portion 130 spanning the fill band-to-band width of the garment. FIG. 28 is a side view.

Figure 29:
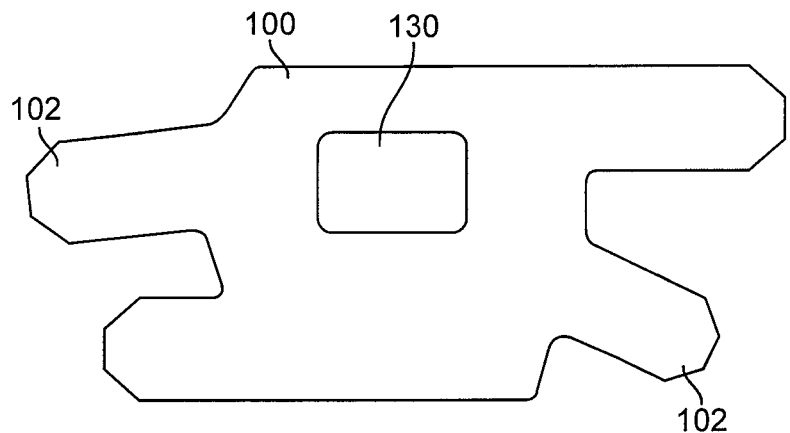
Figure 30:
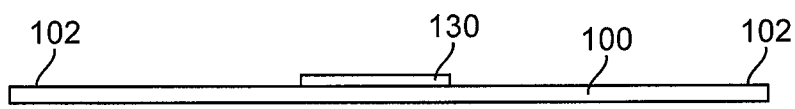

FIG. 29 shows a small second portion 130 attached to a large first portion 100. FIG. 30 is a side view.

Figure 31:
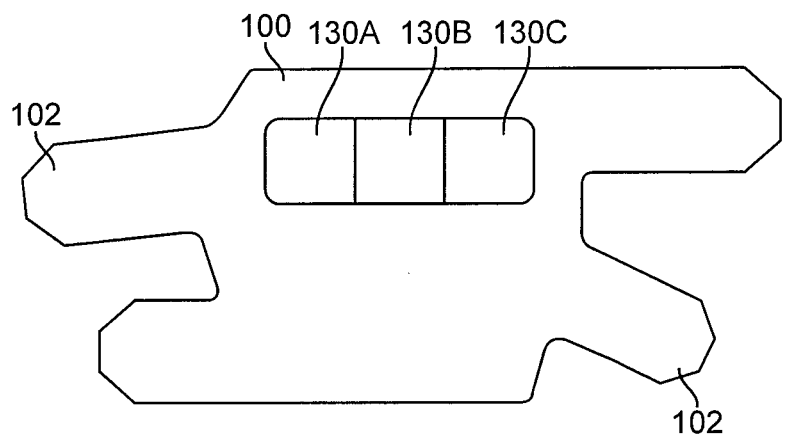
Figure 32:
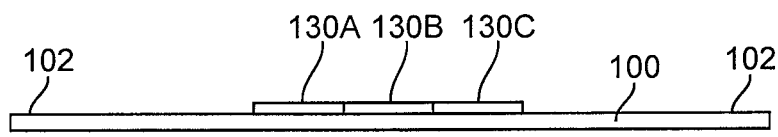

FIG. 31 is an embodiment with three second portions 130A, 130B and 130C attached in series across portion 100. FIG. 32 is a side view.

Figure 33:
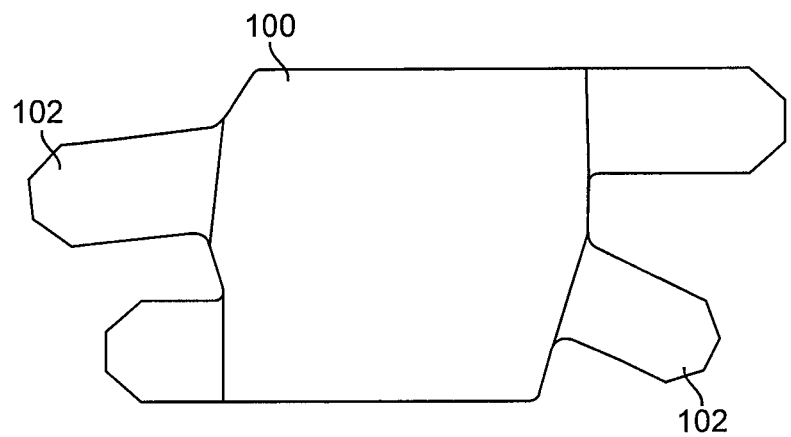
Figure 34:
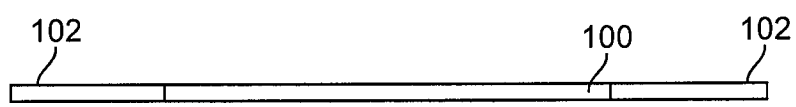

FIG. 33 is an embodiment in which the main body 100 is made of a first material, and the bands 102 are made of a second material having a different stiffness profile. FIG. 34 is a side view. It is to be understood that each band could vary in elasticity, and that they do not all need to be the same.

Figure 35:
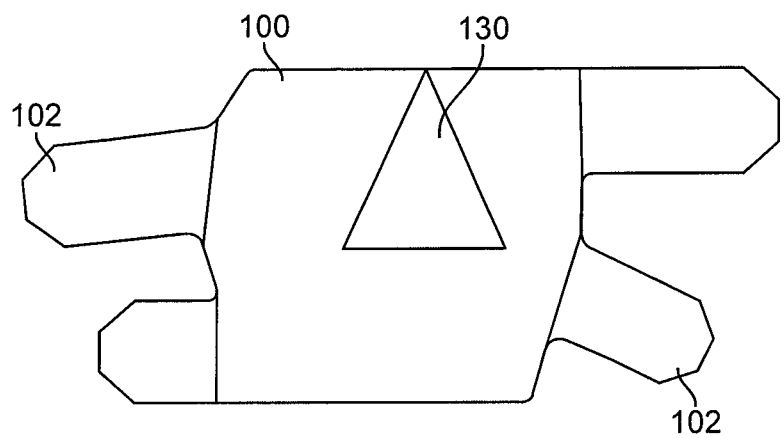
Figure 36:
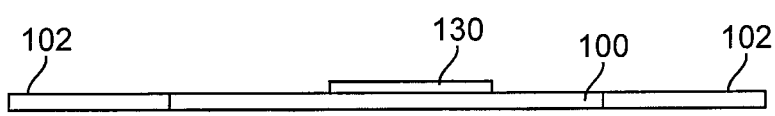

FIG. 35 is an embodiment having a triangular second portion 130 attached onto first portion 100. FIG. 36 is a side view. The inelastic material of 130 would keep the gradient stiffness in the calf while changing the bands would change the stiffness profile of the entire garment.

Figure 37:
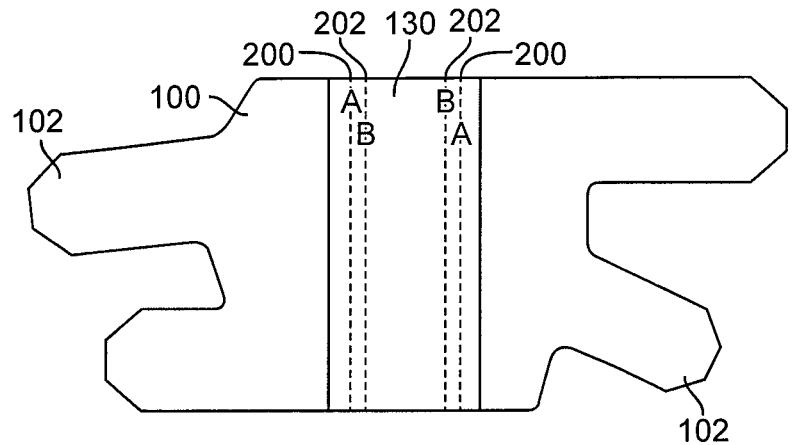
Figure 38:
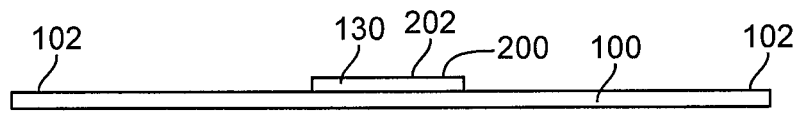

FIG. 37 is an embodiment having first and second indicia 200 and 202 on second portion 130. In use, the second portion 130 can be trimmed along the first or second set of indicia, 200 or 202. Depending on the selected indicia the amount of the second portion remaining will effect the pre-determined range of compression level fluctuation to the body part during wear). FIG. 38 is a side view.

Figure 39:
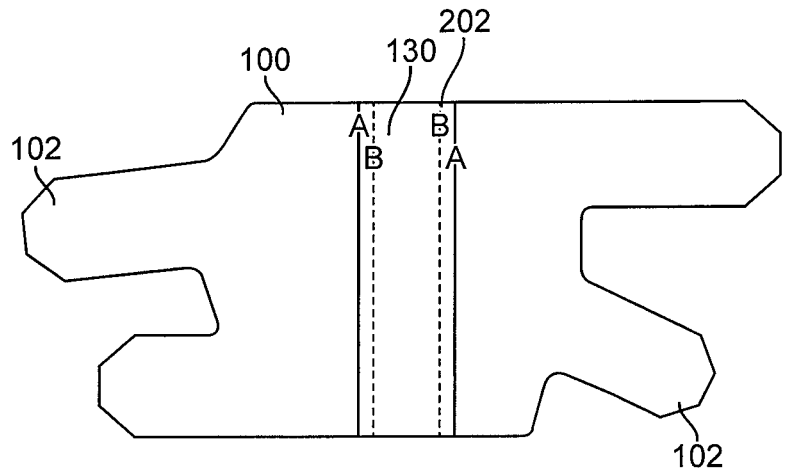
Figure 40:
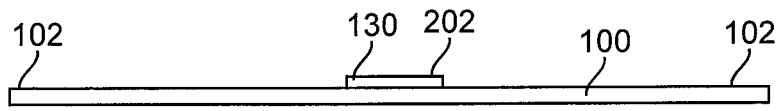

FIG. 39 shows the same embodiment in FIG. 37, however the second portion has been trimmed down to the indicia set labeled 200 in FIG. 37, thus reducing the pre-determined range of compression level fluctuation to the body part during wear, but there are only one set of positioning indicia 202. FIG. 40 is a side view.

Figure 41:
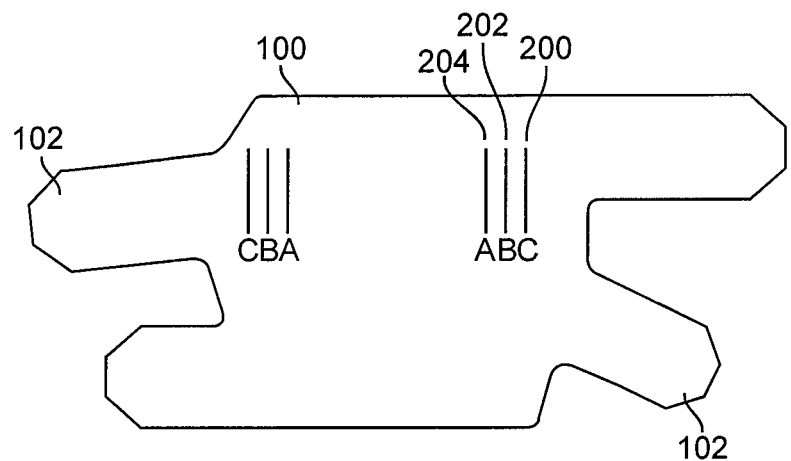
Figure 42:
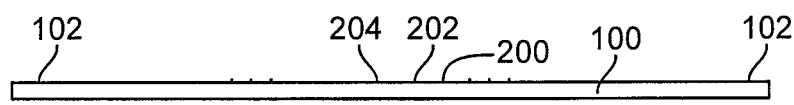

FIG. 41 is an embodiment with indicia 200, 202 and 204 thereon. The indicia indicate how much inelastic material to add to induce the desired compression level fluctuations. FIG. 42 is a side view.

Figure 43:
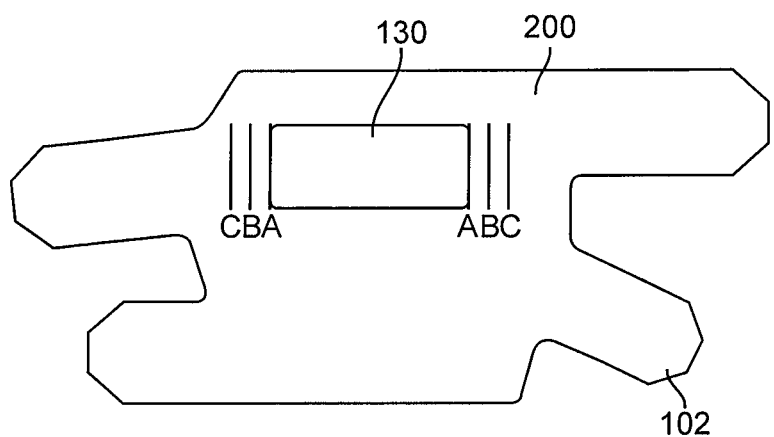
Figure 44:
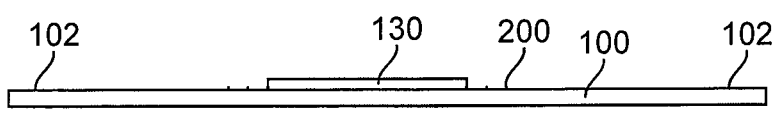

FIG. 43 is similar to FIG. 41, but a second portion 130 has been added. FIG. 44 is a side view. The material of 130 could be trimmed to match the indicia or it could potentially be an elastic material that is stretched and attached to these regions to provide different stiffness before donning the garment.

In the above embodiments of the invention, various compression garments are provided. These compression garments have first and second portions, and the ratio of these portions (and the materials used) around the circumference of the limb is what determines the relative compression force and range of compression force fluctuation that the garment provides.

Preferably, at least one portion comprises indicia thereon, and the placement of the indicia is calibrated such that when the other portion is aligned with the indicia, the compression garment provides the pre-determined base compression force to the body part and/or a compression force fluctuation. Preferably, the indicia display the compression level fluctuation in standard compression units (such as mmHG or PSI). As a result, the user can then select a 30 mmHg mark, align the non-elastic portion with this mark and know the compression level is increasing and decreasing 30 mmHg during wear.

What is claimed is:

1. A method of changing between ranges of compression level fluctuation applied by a compression garment to a body part, a compression level fluctuation range being an absolute change in compression applied to the body part caused by user movement, the method comprising:

selectively dimensioning a first elastic portion of the garment, the first elastic portion having an inner surface for contact with the body part, an outer surface, and an elasticity profile for applying a base level of compression to the body part;

donning the first elastic portion of the garment at least partially around the body part to provide the base level of compression to the body part with a first compression fluctuation range separate from the base level of compression; and then adjusting the garment between ranges of compression level fluctuation while maintaining the base level of compression, by:

selectively dimensioning a second non-elastic portion; and selectively positioning the second non-elastic portion to a defined engagement area of the first elastic portion of the garment by releasably attaching the second non-elastic portion of the garment onto the outer surface of the first elastic portion thereby changing a compression level fluctuation of the garment from the first compression level fluctuation range to a second compression fluctuation range.

2. The method of claim 1, wherein the first elastic portion comprises indicia thereon, and wherein when the second non-elastic portion is aligned with the indicia after the first elastic portion is donned, the compression garment provides one of the ranges of compression level fluctuation to the body part during wear.

3. The method of claim 2, wherein the indicia comprise different sets of indicia, with each set corresponding to a different pre-determined range of compression level fluctuation.

4. The method of claim 1, wherein the defined engagement area of the first elastic portion beneath the second non-elastic portion is a calf region.

5. The method of claim 4, wherein a massaging or pumping fluctuating pressure effect is formed causing inducement of venous blood flow.

6. The method of claim 1, wherein donning the first elastic portion comprises wrapping the first elastic portion fully around a circumference of the body part.

7. The method of claim 1, wherein the first elastic portion is a stocking, and the second non-elastic portion is a band, flap or strap.

8. The method of claim 1, wherein the first elastic portion is a compression wrap having bands operable for wrapping around the body part, and the second non-elastic portion is a band, flap or strap.

9. The method of claim 1, further comprising: positioning indicia on the second non-elastic portion; and aligning the first elastic portion with the indicia so that one of the ranges of compression level fluctuation are applied to the body part during wear.

10. The method of claim 1, further comprising: attaching the second non-elastic portion onto the outer surface of the first elastic portion by hook and loop fasteners after the first elastic portion is wrapped around the body part.

11. The method of claim 1, further comprising: trimming the the second non-elastic portion along one or more indicia between top and bottom edges of the second non-elastic portion.

12. The method of claim 1, wherein the first compression level fluctuation range is between 0 and 10 mmHG and the second compression level fluctuation range is between 10 and 20 mmHG, 20 and 30 mmHg, or 30 and 40 mmHg.

13. The method of claim 1, wherein the second compression level fluctuation range consists of 10 mmHg to 20 mmHg, 20 mmHg to 30 mmHg, or 30 mmHg to 40 mmHg.

14. The method of claim 1, wherein adjusting the garment between ranges of compression level fluctuation further comprising: trimming the second non-elastic portion.

15. A method of adjusting compression level fluctuation of a compression garment while maintaining a base level of compression, a compression level fluctuation range being an absolute change in compression applied to the body part caused by user movement, the method consisting of:

in a first step, selectively dimensioning a first elastic portion of the garment, the first elastic portion having an inner surface for contact with the body part and an outer surface;

in a second step, donning the first elastic portion of the garment at least partially around the body part to provide the base level of compression to the body part; and then in a third step, adjusting the garment between one of a plurality of pre-determined dynamic ranges of compression level fluctuation by:

selectively dimensioning a second non-elastic portion, the second non-elastic portion being operable to be wrapped at least partially around the first elastic portion;

selecting an engagement area of the first elastic portion to releasably receive the second non-elastic portion; and selectively positioning the second non-elastic portion to the engagement area by releasably attaching the second non-elastic portion of the garment onto the outer surface of the first elastic portion that is wrapped around the body part thereby changing a first compression level fluctuation of the garment to a second compression level fluctuation, wherein the second compression level fluctuation is at least 5 mmHG greater than the first compression level fluctuation.

* * * * *